US012778878B2

(12) United States Patent
Imbert et al.

(10) Patent No.: US 12,778,878 B2
(45) Date of Patent: Nov. 3, 2026

(54) METHOD FOR OBTAINING AN EXTRACT OF PATCHOULI LEAVES AND COSMETIC USES THEREOF

(71) Applicants: ISP INVESTMENTS LLC, Wilmington, DE (US); JAFER ENTERPRISES R&D, S.L.U, Granollers (SE)

(72) Inventors: Isabelle Imbert, Cannes (FR); Corinne Coquet, Cipieres (FR); Catherine Gondran, Callian (FR); Florian Labarrade, Antibes (FR); Jeremie Borsotto, Pegomas (FR); Sebastien Garnier, Le Rouret (FR); Leslie Duroure, Mouans-Sartoux (FR)

(73) Assignees: ISP INVESTMENTS LLC, Wilmington, DE (US); JAFER ENTERPRISES R&D, S.L.U, Granollers (SE)

( * ) Notice: Subject to any disclaimer, the term of this patent is extended or adjusted under 35 U.S.C. 154(b) by 1207 days.

(21) Appl. No.: 17/426,986

(22) PCT Filed: Jan. 27, 2020

(86) PCT No.: PCT/EP2020/051883
§ 371 (c)(1),
(2) Date: Jul. 29, 2021

(87) PCT Pub. No.: WO2020/156981
PCT Pub. Date: Aug. 6, 2020

(65) Prior Publication Data

US 2022/0096361 A1 Mar. 31, 2022

(30) Foreign Application Priority Data

Jan. 29, 2019 (FR) ...................................... 1900813

(51) Int. Cl.

| | |
|---|---|
| ***A61K 8/9789*** | (2017.01) |
| ***A61K 8/34*** | (2006.01) |
| ***A61K 8/63*** | (2006.01) |
| ***B01D 11/02*** | (2006.01) |

(52) U.S. Cl.
CPC ............ *A61K 8/9789* (2017.08); *A61K 8/347* (2013.01); *A61K 8/63* (2013.01); *B01D 11/0203* (2013.01); *B01D 11/0284* (2013.01); *B01D 11/0288* (2013.01); *B01D 11/0292* (2013.01)

(58) Field of Classification Search
None
See application file for complete search history.

(56) References Cited

U.S. PATENT DOCUMENTS 6,387,416 B1 5/2002 Newmark et al.
2014/0271525 A1 9/2014 Florence

FOREIGN PATENT DOCUMENTS

CN 101485647 B 4/2013
CN 108096315 A * 6/2018 ............ A61K 38/08
JP 2014-091772 A2 5/2014
WO 2018/0167038 A1 9/2018

OTHER PUBLICATIONS

Monroy et al. Influence of ethanol, water, and their mixtures as co-solvents of the supercritical carbon dioxide in the extraction of phenolics from purple corn cob (*Zea mays* L.) J. Supercritical Fluids 2016, 118, 11-18 (Year: 2016).*
Allwar et al. "Removal of Fe and Cu Ions from Patchouli Essential Oil Using ZnCl2-Activated Carbon Adsorbent Modified With Ammonia" IOSR Journal of Applied Chemistry 2015, 8, 17-23 (Year: 2015).*
NIH "Stearyl Alcohol" 2024, National Library of Medicine, PubChem, https://pubchem.ncbi.nlm.nih.gov/compound/Stearyl-Alcohol (accessed Oct. 10, 2024) (Year: 2024).*
Muttucumaru "Alcohol-should your skincare be teetotal?" Aug. 20, 2017, Get the Gloss, https://www.getthegloss.com/beauty/skincare/alcohol-should-your-skincare-be-teetotal (accessed Oct. 7, 2024) (Year: 2017).*
Donelian et al. "Comparison of extraction of patchouli (*Pogostemon cablin*) essential oil with supercritical CO2 and by steam distillation" J. Supercritical Fluids 2009, 48, 15-20 (Year: 2009).*
Soh et al. "A study of essential oil extraction and antioxidant activity of patchouli (*Pogostemon cablin*) using supercritical carbon dioxide" ON12 2018, 1-8 (Year: 2018).*
Buschhaus et al. "Chemical Composition of the Epicuticular and Intracuticular Wax Layers on Adaxial Sides of Rosa canina Leaves" Annals of Botany 2007, 1-8 (Year: 2007).*
References cited in the International Search Report of International Application No. PCT/US2020/051883.
Lin Rong-Feng et al: "Prevention of UV radiation-induced cutaneous photoaging in mice by topical administration of patchouli oil", Journal of Ethnopharmacology, Elsevier Ireland Ltd, IE, vol. 154, No. 2, Apr. 18, 2014 (Apr. 18, 2014), pp. 408-418—XP029028509.
Donelian A et al: "Comparison of extraction of patchouli (Pogostemon cablin) essential oil with supercritical CO"2 and by steam distillation", The Journal of Supercritical Fluids, Elsevier, Amsterdam, NL, vol. 48, No. 1, Feb. 1, 2009 (Feb. 1, 2009), pp. 15-20, XP025924407.
Gondran C et al: "Evaluation of an extract of *Pogostemon cablin* (patchouli) on the cannabinoid receptor CB2 and associated reduction of skin discomfort sensation", Journal of Investigative Dermatology, vol. 139, No. 9, Suppl. S, Sep. 2019 (Sep. 2019), p. S260, & 49th Annual Meeting of the European-Society-Fordermatological-Research (ESDR); Bordeaux, France; Sep. 18 -21, 2019.

* cited by examiner

*Primary Examiner* — Bethany P Barham
*Assistant Examiner* — Judith Marie Kamm
(74) *Attorney, Agent, or Firm* — Aseem Mehta; Nathalie Tietcheu

(57) ABSTRACT

The invention relates to a method for obtaining an extract of patchouli leaves comprising a supercritical carbon dioxide extraction and a co-solvent such as ethanol. The invention also relates to a patchouli extract obtainable by the method of the invention, a composition comprising such an extract, and the cosmetic use of a composition according to the invention for care of the skin, the scalp and the appendages.

7 Claims, 3 Drawing Sheets

(mean ± SEM; n=3)
***: highly significant; *: significant as per Student's t test (mean ± SEM; n=3)
***: highly significant; *: significant; ns: not significant as per Student's t test (mean ± SEM; n=3)
*: highly significant; : very significant as per Student's t test (mean± SEM; n=3)
***: highly significant; *: significant as per Student's t test

METHOD FOR OBTAINING AN EXTRACT OF PATCHOULI LEAVES AND COSMETIC USES THEREOF

CROSS-REFERENCE

This application is a National Stage filing of International Application No. PCT/EP2020/051883, filed on Jan. 27, 2020, which claims priority of French Patent Application No. FR1900813A, filed on Jan. 29, 2019, which are hereby incorporated by reference herein in their entireties.

TECHNICAL FIELD

The present invention relates to the field of cosmetics and more particularly to the field of active ingredients for the formulation of skin-care compositions. The invention relates to a method for obtaining a particular extract from leaves of patchouli (*Pogostemon cablin*). The invention also relates to extracts of patchouli leaves comprising from 50 to 80% of volatile compounds, from 2 to 5% of phenolic compounds and from 15 to 48% of lipid compounds obtained by such a method, to cosmetic compositions comprising such extracts, and finally to the cosmetic use of such compositions for the care of the skin, the scalp and the appendages.

TECHNICAL BACKGROUND OF THE INVENTION

Patchouli (*Pogostemon cablin*) is a tropical plant of the Lamiaceae family, mainly cultivated in Asia and particularly in Indonesia; it is about 1 metre high, with large, velvety leaves. After drying, patchouli has a powerful, woody and earthy scent with smoky and camphorated accents.

Patchouli is mainly used in perfumery and cosmetics, in the form of essential oil produced by simple distillation of the leaves or by more complex extraction techniques. For example, a method for obtaining patchouli essential oil derivatives by distillation repeated 2 to 4 times, then addition of hexane and final concentration by chromatography is known from document KR1034010B1. A method for extracting patchouli oil is also known, comprising a step of microbial treatment of dry patchouli leaves and stems (U.S. Pat. No. 7,879,584B2).

The major compounds in patchouli essential oils are patchoulol, gamma-guaiene, alpha-guaiene, alpha-patchoulene and beta-caryophyllene. An essential oil obtained by steam extraction contains 30% to 40% patchoulol among dozens of other compounds (Donelian A. et al. Comparison of extraction of patchouli (*Pogostemon cablin*) essential oil with supercritical $CO_2$ and by steam distillation; J. Supercritical Fluids 48 (2009) 15-20).

Patchouli essential oil also includes, according to studies by Yahya and Yunus (Yahya, A and Yunus R, Influence of sample preparation and extraction time on chemical composition of steam distillation derived patchouli oil. Procedia Engineering, 2013; 53: 1-6) sesquiterpenes: alpha-bulnesene (20-25%), alpha-guaiene (10-12%), beta-patchoulene (2-3%), beta-caryophyllene (3-4%) and sesquiterpene alcohols such as pogostol (2-3%).

Patchouli is known and used in Ayurvedic medicine for comforting the mind and reconnecting with the inner self (Swamy M K et al. A Comprehensive Review on the Phytochemical Constituents and Pharmacological Activities of *Pogostemon cablin* Benth: An Aromatic Medicinal Plant of Industrial Importance. Molecules. 2015 May 12; 20(5): 8521-47). In the West, it is associated with the hippie movement of the 1970s.

In aromatherapy, patchouli is used to relax and relieve depression (Ramya H. G. et al. An introduction to patchouli (*Pogostemon cablin* Benth.)—A medicinal and aromatic plant: It's importance to mankind. July, 2013 Agric Eng Int: CIGR Journal Open access at http://www.cigrjournal.org Vol. 15, No. 2 243) and also as a tonic, digestive stimulant and circulatory tonic.

Patchouli is also known to be anti-inflammatory, anti-emetic, analgesic and antiseptic and is known for its effects on the skin and hair. For example, a composition for promoting hair growth prepared by hydroalcoholic maceration of the dry leaves of *Pogostemonis, Helianthus annus* and *Cinnamoni cortex* plants, cited in patent document KR2008081393A, and a patchouli-based cleansing composition obtained by supercritical extraction and polyglucosides of natural origin, described in document WO2010086717, are known.

Patchouli essential oil is also known to prevent photoageing due to its antioxidant properties (Lin R F. Prevention of UV radiation-induced cutaneous photoaging in mice by topical administration of patchouli oil; J Ethnopharmacol. 2014 Jun. 11; 154(2):408-18).

The skin is an organ composed of several layers (dermis, epidermis and stratum corneum), which covers the entire surface of the body and ensures protective functions against external aggressions, as well as sensory, immune, metabolic, thermoregulatory or even barrier functions, limiting dehydration.

The appearance of the skin can be modified by internal changes (natural ageing, diseases and hormonal changes such as pregnancy) or external factors (environmental factors, such as pollution, sunlight, pathogens, temperature variations, etc.). All of these alterations affect not only the skin, but also the keratinous appendages such as hair, eyelashes, eyebrows, nails and hair.

The endogenous cannabinoid or endocannabinoid system takes its name from the plant that led to its discovery—*cannabis*. This system is present in all vertebrates, in many organs where it is involved in the regulation of a very wide range of physiological processes, including neural development, inflammation, immunity, appetite, metabolism, perception of sensory information, especially nociceptive information, sleep/wake cycles, and regulation of stress and emotional state.

The skin and its appendages (hair follicle, sebaceous gland) have their own complete and functional cannabinoid system, including endocannabinoid ligands, their CB1 and CB2 receptors associated with G proteins, as well as their enzymes of synthesis and metabolism (Ashton J C et al.; Tamás Bíró, Balázs I. Tóth, 1 György Haskó, Ralf Paus and Pal Pacher. The endocannabinoid system of the skin in health and disease: novel perspectives and therapeutic opportunities. Trends Pharmacol Sci. 2009 August; 30(8): 411-420). The endocannabinoid system of the skin is particularly involved in the regulatory functions of epidermal cell proliferation and differentiation, and in the modulation of inflammation. In addition, CB2 receptor agonists stimulate the synthesis of beta-endorphin, known for its pain-relieving effect (Su et al. Cannabinoid CB2 Receptors Contribute to Upregulation of b-endorphin in Inflamed Skin Tissues by Electroacupuncture. Molecular Pain 2011, 7:98. Ibrahim M. M. CB2 cannabinoid receptor activation produces antinociception by stimulating peripheral release of endogenous opioids. Proc Natl Acad Sci USA. 2005, February 22, vol. 102, no. 8, 3093-3098).

New molecules acting on CB2 receptors, thus not related to the psychotropic effect, have been recently developed (Klein T W. Cannabinoid-based drugs as anti-inflammatory therapeutics. Nature reviews. 2005 May; 5, 400-411). Exogenous cannabinoids can also be used topically for their anti-inflammatory properties (Mounessa J S, Siegel J A, Dunnick C A, Dellavalle R P. The role of cannabinoids in dermatology. J Am Acad Dermatol. 2017 July; 77(1):188-190). This anti-inflammatory activity has also been reported for THC (Δ9-tetrahydrocannabinol), the main component of *Cannabis sativa*. THC can exert an anti-inflammatory and pain-relieving effect via the CB1 and CB2 cannabinoid receptors. The psychotropic effect of THC is mediated by CB1 cannabinoid receptors.

In the field of cosmetics, the development of new plant extracts that can act on the skin's endocannabinoid system and have soothing effects is also of great interest.

The inventors have thus demonstrated that a particular new patchouli extract, obtained by an extraction method allowing the extraction of volatile compounds, phenolic compounds and lipid compounds at the same time, has soothing and protective effects on the skin and hair. The extract of the invention is different from a conventional patchouli essential oil in its content of phenolic compounds, represented by a mixture of non-glycosylated flavonoids, and of lipid compounds, represented mainly by a mixture of fatty acids, phytosterols, triterpenes and acyl glycerides. It has been found that this particular composition of the extract has enhanced biological activity compared to a conventional patchouli essential oil.

SUMMARY OF THE INVENTION

The first object of the invention is a method for obtaining an extract of dried patchouli leaves comprising the following steps:

a) The upper part of the patchouli aerial parts is harvested and then dried and ground or cryogenically ground.
b) A supercritical carbon dioxide extraction is performed in the presence of a polar co-solvent, such as a hydroalcoholic solution of ethanol, at a concentration of between 50 and 96% in water (volume/volume).
c) The patchouli extract is recovered and decoloured in the presence of activated carbon and filtered before the co-solvent is evaporated.
d) The crude extract obtained in step c) is solubilised in a saturated or unsaturated, linear or branched fatty alcohol solvent comprising from 8 to 30 carbon atoms to obtain a concentration of crude extract in the final extract of between 2 and 6% by weight of the total weight of the solubilised extract.

The second object of the invention is a crude patchouli extract obtainable by the method according to the invention comprising between 50 and 80% of volatile compounds mainly of the sesquiterpene and sesquiterpene alcohol type, between 2 and 5% of non-glycosylated flavonoid-type phenolic compounds, and between 15 and 48% of lipid compounds such as fatty acids and phytosterols.

The invention also relates to a solubilised extract of patchouli comprising from 2 to 6% of crude extract solubilised in a saturated or unsaturated, linear or branched fatty alcohol solvent comprising from 8 to 30 carbon atoms.

The third object of the invention is a cosmetic composition for the care of the skin, the scalp and the appendages, comprising, as active substance, a patchouli extract obtained according to the method of the invention and a physiologically acceptable medium.

The fourth object of the invention is the cosmetic use of a composition comprising the patchouli extract of the invention to improve the appearance of the skin, to combat the signs of skin ageing or to improve the hydration of the skin and reinforce the barrier function or soothe the skin.

BRIEF DESCRIPTION OF THE DRAWINGS

The invention and its advantages will be better understood from the following description and non-limiting embodiments, illustrated with reference to the attached drawings in which:

FIG. 1 shows the effect of the patchouli extract on IL1-R1 levels assessed in skin biopsies after UVB irradiation FIG. 2—Quantification of IL1-R1 (interleukin-1 receptor) labelling on skin biopsies exposed to UVB and treated with patchouli extract or patchouli essential oil

DETAILED DESCRIPTION OF THE INVENTION

Extraction Method

Figure 1:
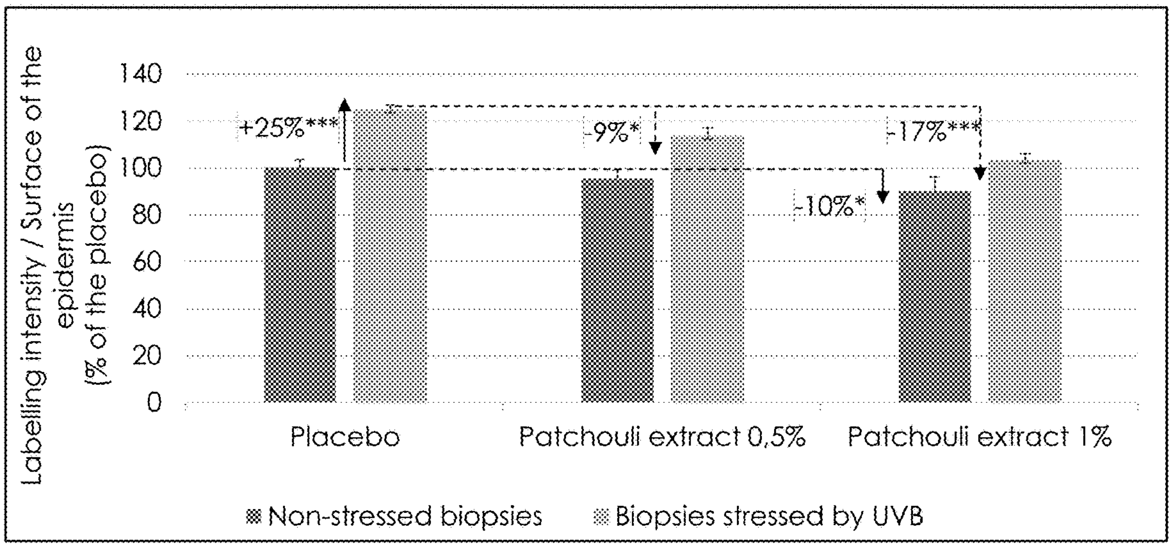
FIG. 1—Quantification of IL1-R1 (interleukin-1 receptor) labelling on skin biopsies exposed to UVB and treated with patchouli extract

Extraction methods for patchouli using supercritical $CO_2$ are described in several documents. Document CN101485647B (also published as WO2010096987) describes a patchouli extract extracted by alcohol or supercritical $CO_2$ and new pharmaceutical uses. Patchouli is powdered and subjected to extraction by supercritical $CO_2$ under the following conditions: pressure 12-30 Mpa; temperature 55-60° C. These patchouli extracts contain patchouli alcohol (patchoulol).

Also known is document 1N20090019511 (also published as WO2010086717) which describes a herbal cleansing composition comprising certified organic plant extracts obtained by supercritical extraction and polyglucosides of natural origin.

Donelian A. and colleagues (J. Supercritical Fluids 48 (2009) 15-20) describe a supercritical $CO_2$ extraction of dried and ground Patchouli leaves under the following conditions: temperatures 40 and 50° C., pressures 8.5 and 14 MPa, and $CO_2$ flow $6.0\times10^{-3}$ kg/min, for a period of 340 min. Chromatographic analyses show that the extraction conditions at 14 MPa at 40° C., produce the most concentrated patchoulol essential oil and the highest extraction yield.

It is known from the work of Hybertson B. M. (J Chem Eng Data. 2007 Jan. 1; 52(1)) that the level of patchoulol extracted by supercritical $CO_2$ varies with the temperature and pressure applied. The conditions giving the highest concentration of patchoulol are 40° C., and 25 MPa. A fluid is said to be supercritical when it is placed under conditions of temperature and pressure beyond its critical point (Tc, Pc). The physical properties of a supercritical fluid (density, viscosity, diffusion, diffusivity) are intermediate between those of liquids and gases, but their dissolution properties are considerably enhanced. It is well known to use carbon dioxide in the supercritical state because it has the advantage of being a totally neutral, non-toxic, non-flammable solvent that can be used at a fairly low temperature (31° C.) for a pressure higher than its critical pressure of 73.8 bar. This technique makes it possible to work at a moderate temperature (from 31° C.), which does not alter the organoleptic qualities and active ingredients of the extract obtained. Moreover, after evaporation of the $CO_2$ returned to the gaseous state, it is possible to obtain extracts free of any residue of the extraction solvent. It is also possible to use other fluids, such as argon.

However, no document in the prior art describes the extraction method of the invention using both carbon dioxide in the supercritical state and an ethanol/water solution as solvent.

The extraction method of the invention uses the upper part of the dried aerial parts of patchouli, comprising the following steps:

a) The upper part of the patchouli aerial parts is harvested and then dried and ground or cryogenically ground.
b) A supercritical carbon dioxide extraction is performed with the addition of a polar co-solvent such as a hydroalcoholic solution of ethanol at a concentration of between 50 and 96% in water (volume/volume).
c) The patchouli extract is recovered and decoloured in the presence of activated carbon and filtered before the co-solvent is evaporated.
d) The crude extract obtained is solubilised in a saturated or unsaturated, linear or branched fatty alcohol solvent comprising 8 to 30 carbon atoms.
e) The extract obtained in step c) or d) may possibly be purified.

The upper part of the patchouli aerial parts is harvested, then the leaves and the finest stems are dried and ground or cryogenically ground.

The term "upper part of the aerial parts" is defined as the leaves and thinnest stems, after discarding plant material in poor condition and stems that are too large.

For the purposes of this description, "upper part of the aerial parts" does not include fruits, flowers or seeds.

In the course of this description, the terms "upper parts of the aerial parts" and "leaves" will be used interchangeably to refer to the leaves and the thinner stems.

Preferably, the extract is obtained from the *Pogostemon cablin* plant grown in Colombia.

To carry out step a) the upper part of the patchouli aerial parts is harvested and then dried. Preferably, the leaves and stems are cryogenically ground in a knife mill with a 4 mm grid, which makes it possible to obtain a powder with a particle size of between 100 and 800 μm, advantageously between 300 and 600 μm, and more preferably between 400 and 500 μm.

To carry out step b) the fluid in the supercritical state is chosen from carbon dioxide and argon, although carbon dioxide is preferred.

According to a preferred embodiment, in step b):

A polar co-solvent such as an ethanol-based hydro-alcohol solution.

Preferably, the ethanol is at a concentration of between 60 and 80% (volume/volume in water) and even more preferably the ethanol is at a concentration of 70% (70% volume/volume in water).

The extraction temperature in step b) is between 35 and 70° C., advantageously between 40 and 65° C. and preferably between 50 and 60° C.

The pressure within the extractor is between 90 and 1000 bar, preferably between 160 and 800 bar and even more preferably between 230 and 700 bar.

The weight ratio of supercritical solvent (carbon dioxide) to the quantity of raw material used (dried and ground patchouli leaves) is between 10 and 70, advantageously between 25 and 55, and preferably between 30 and 50.

Advantageously, to carry out step b), the powder obtained in step a) is placed in a stainless steel cartridge, the cartridge is placed in a supercritical fluid extractor. The solvent used for extraction is carbon dioxide in the supercritical state. At the same time, a co-solvent such as ethanol is also injected into the extraction cartridge. The weight ratio of carbon dioxide to co-solvent is about 15.

In step c) the extract obtained in step b) is decoloured in the presence of activated carbon and then filtered. The ethanol/water co-solvent is evaporated. The extraction yield is thus close to 6%.

At this stage, the crude extract of patchouli leaves is in paste form and comprises between 50 and 80% volatile compounds, between 2 and 5% phenolic compounds and between 15 and 48% lipid compounds.

In step d) the crude extract is solubilised in an agro-sourced solvent such as a saturated or unsaturated, linear or branched fatty alcohol comprising 8 to 30 carbon atoms.

Preferably, the fatty alcohol solvent is octyldodecanol capable of solubilising all the families of compounds described in the extract. After this solubilisation step, the extract is in the form of a clear, fluid solution containing between 2 and 6% of crude Patchouli leaf extract.

Preferably, the solubilised extract contains 4% crude extract of Patchouli leaves.

Octyldodecanol is used as a solvent and as a cosmetically acceptable liquid carrier for the compounds of interest. Agro-sourced refers to molecules that are totally or partially derived from biomass, as these solvents are composed of renewable carbon.

Optionally, a step e) of purification of the extract obtained in step c) can be carried out by any technique known to a person skilled in the art and in particular by chromatography or by molecular distillation.

Extract

The extract that can be obtained by the method after solubilisation in step d) is in liquid form and contains a mixture of molecules of interest with very different polarities. Analysis of the extract shows that the extracted molecules are different in quality and quantity from those described in the prior art. The extract of the invention is different from a conventional patchouli essential oil in its content of phenolic compounds, such as flavonoids, and lipid compounds, such as phytosterols and fatty acids.

However, it has been demonstrated in example 7 of the present application that this extract has a greater efficacy in soothing the skin than a conventional patchouli essential oil.

Thus, the second subject of the invention is a patchouli extract obtainable by the method according to the invention.

The term "crude extract" of patchouli means the extract in paste form obtained in step b) of the method.

The term "patchouli extract" or "solubilised extract" in the sense of the invention means the liquid extract obtained after solubilisation in step c) of the method.

The extract thus obtained according to the invention is a clear, pale yellow solution with an oily consistency.

Patchouli extract is composed in particular of:

2 to 6% by weight of crude extract in relation to the total weight of the solubilised extract, preferably, 4% by weight of crude extract in relation to the total weight of the patchouli extract.

The raw extract itself includes:

from 50 to 80% of volatile compounds (mainly sesquiterpenes and sesquiterpene alcohols), advantageously from 55 to 75% and preferably from 60 to 70%.

2 to 5% phenolic compounds (mainly non-glycosylated flavonoids), advantageously 2.5 to 4.5% and preferably 3 to 4%.

15 to 48% of lipid compounds (in particular fatty acids, phytosterols, triterpenes, acyl glycerides), advantageously from 20.5 to 42.5% and preferably from 26 to 32%.

In a very advantageous embodiment, the crude extract comprises 65% volatile compounds, 3.5% phenolic compounds and 31.5% lipid compounds.

The term "volatile compounds" means molecules that are light enough to be detected by gas chromatography. These are mainly sesquiterpenes and sesquiterpene alcohols with the respective empirical formulae $C_{15}H_{24}$ and $C_{15}H_{26}O$ present in the extract The term "phenolic compounds" means non-glycosylated flavonoids detected in the extract.

The term "lipid compounds" means the group of molecules of a polar nature belonging to the families of fatty acids, triterpenes, sterols and acyl glycerides present in the extract.

Each fraction of the raw extract was analysed to determine the main molecules that may have biological activity on the skin.

The volatile compounds were analysed by gas chromatography (GC) coupled to a mass spectrometry (MS) detector and/or flame ionisation detector (FID). Validation of identifications was made possible by comparing linear retention indices and mass spectra contained in libraries. Quantification by GC/FID is done by internal calibration using predicted and calculated response factors.

The phenolic and lipid compounds were monitored by high performance liquid chromatography (HPLC) injection coupled with an evaporative light scattering detector (ELSD). Identifications were confirmed by nuclear magnetic resonance (NMR) and/or MS analysis of the isolated compounds with confirmation by injection of standards when possible. Flavonoids were measured with a diode array detector (DAD/UV) by internal calibration with gallic acid. After validation of the lipid profile conformity, the global lipid content (fatty acids, sterols, triterpenes, acyl glycerides, etc.) was estimated by subtraction of the volatile and flavonoid contents.

The main molecules identified were:

In the volatile fraction, sesquiterpene and sesquiterpene alcohol compounds such as alpha-guaiene, alpha-bulnesene, and patchoulol.

In the phenolic fraction, non-glycosylated flavonoid compounds such as pachypodol.

In the lipid fraction, compounds of the fatty acid type (such as linolenic, linoleic, and palmitic acids), phytosterols (such as β-sitosterol and stigmasterol, etc.), triterpenes (such as oleanolic acid) and acylglycerides.

The non-exhaustive list of compounds present in each of the fractions is given in the following Table 1:

| Chemical family | Identification |
|---|---|
| Volatile compounds (in particular sesquiterpenes and sesquiterpene alcohols) Fraction A | Alpha bulnesene |
| | Patchoulol |
| | Pogostol |
| | Alpha guaiene |
| | Beta patchoulene |
| | Beta caryophyllene |
| | Seychellene |
| | Alpha patchoulene |
| | Norpatchoulenol |
| Phenolic compounds (in particular flavonoids) - Fraction B | Pachypodol |
| | 5-hydroxy-7,3',4'-trimethoxyflavanone |
| | Rhamnetine |
| | Rhamnazine |
| | Retusine |
| | 4',5-dihydroxy-3',7-dimethoxyflavanone |
| | 3,5-dihydroxy-4',7-dimethoxyflavone |
| | 5-hydroxy-3,4',7'-trimethoxyflavone |
| Lipid compounds (in particular fatty acids, sterols, triterpenes, acyl glycerides) - Fraction C | Linolenic acid |
| | Oleanolic acid |
| | Linoleic acid |
| | Methyl linoleate |
| | Palmitic acid |
| | Oleic acid |
| | Stearic acid |
| | Beta sitosterol |
| | Stigmasterol |
| | Acyl glycerides |

It was possible to quantify some markers of the crude extract. This contained in particular:

16.1 to 25.7% patchoulol co-eluted with pogostol, advantageously 17.7 to 24.1%, preferably 19.3 to 22.5% (Fraction A).

10.2 to 16.2% ⊠-bulnesene, advantageously 11.2 to 15.2%, preferably 12.2 to 14.2% (Fraction A).

7.0 to 11.0% ⊠-guaiene, advantageously 7.6 to 10.4%, preferably 8.3 to 9.7% (Fraction A).

1 to 2.6% pachypodol co-eluted with 5-hydroxy-7,3',4'-trimethoxyflavanone, advantageously 1.3 to 2.3% and preferably 1.55 to 2.05% (Fraction B).

Cosmetic Compositions

The third object of the invention is a composition comprising, as a soothing and anti-ageing active substance, an effective amount of a patchouli extract according to the invention, and a physiologically acceptable medium.

In this description, unless otherwise specified, it is understood that when an interval is given, it includes the upper and lower bounds of the interval.

In this description, unless otherwise specified, percentages are given by weight.

Another object of the invention relates to a composition comprising, as an anti-ageing active substance, an effective amount of a patchouli extract obtainable by the method according to the invention, and a physiologically acceptable medium.

A "physiologically acceptable medium" means a vehicle suitable for contact with the outer layers of the skin, scalp or appendages, without toxicity, irritation, undue allergic or similar response or intolerance reaction, and commensurate with a reasonable benefit/risk ratio.

Examples of physiologically acceptable media commonly used in the intended field of application are formulation excipients such as solvents, thickeners, thinners, antioxidants, colouring agents, sunscreens, self-tanning agents, pigments, fillers, preservatives, perfumes, odour absorbers, essential oils, vitamins, essential fatty acids, surfactants, film-forming polymers, etc.

Preferably, the composition according to the invention comprises the patchouli extract obtainable by the method according to the invention at a concentration of 0.1 to 10% by weight in relation to the total weight of the composition, preferably 0.5% to 5%, and a physiologically acceptable medium.

The composition usable according to the invention may be applied by any suitable route, in particular externally and topically, and the formulation of the compositions will be adapted by a person skilled in the art.

Preferably, the compositions according to the invention are in a form suitable for topical application.

The term "topical application" means applying or spreading a composition comprising the patchouli extract of the invention on the surface of the skin, scalp, mucosa or appendages.

The term "skin" refers to the skin of the face, in particular the eye area and mouth, the nose, the forehead, the neck, the hands, but also the skin of the whole body, including the scalp.

The compositions according to the invention are particularly suitable for topical application to healthy skin. In the context of the present invention, "healthy skin" is understood to mean skin which does not have any skin pathology.

The term "appendages" refers to the keratinised skin appendages present in humans and animals, rich in keratin, and more particularly head and body hair, eyelashes, eyebrows and nails.

The topical compositions for implementing the invention may in particular be in the form of an aqueous, hydroalcoholic or oily solution, an oil-in-water emulsion, a water-in-oil emulsion, a multiple emulsion, a micro-emulsion, a nano-emulsion or any colloidal system that can be used in cosmetics; they may also be in the form of suspensions or powders suitable for application to the skin, mucous membranes, lips and/or hair.

These compositions may be more or less fluid and may also be in the form of a cream, lotion, milk, serum, ointment, gel, paste or foam. They may also be in solid form, for example in the form of a stick, or may be formulated to be compatible with aerosol delivery.

In all cases, a person skilled in the art will ensure that the excipients and their proportions are chosen in such a way as not to impair the advantageous properties sought of the composition according to the invention. These excipients may, for example, correspond to 0.01 to 20% of the total weight of the composition. When the composition according to the invention is an emulsion, the fatty phase may represent from 5 to 80% by weight and preferably from 5 to 50% by weight in relation to the total weight of the composition. The emulsifiers and co-emulsifiers used in the composition are chosen from those conventionally used in the field in question. For example, they may be used in a proportion ranging from 0.3 to 30% by weight relative to the total weight of the composition.

In a particular embodiment, the compositions may contain one or more additional active substances to enhance the effect of the patchouli extract according to the invention.

The INCI Dictionary & Handbook ("International Nomenclature of Cosmetic Ingredients 13th Ed. 2010" published by the Personal Care Products Council, Inc., Washington, D.C.) describes a wide variety, without limitation, of cosmetic ingredients commonly used in the skin-care industry, which are suitable for use as additional active substances in the compositions according to the present invention.

Non-limiting examples of these classes of additional active substances include: anti-ageing agents, anti-wrinkle agents, moisturising agents, softening agents, keratolytic or desquamating agents, anti-seborrhoeic agents, anti-dandruff agents, agents modulating skin cell differentiation or proliferation, agents modulating skin pigmentation, self-tanning agents, anti air pollution agents, anti-glycation agents, firming agents, aquaporin synthesis stimulating agents, agents stimulating the synthesis of lipids and stratum corneum components (ceramides, fatty acids), adipocyte proliferation stimulating agents, glycosaminoglycan synthesis stimulating agents, DNA repairing agents, DNA protecting agents, agents for the treatment and/or care of sensitive skin firming agents, anti-stretch mark agents, astringent agents, dermo-relaxing agents, cytokine growth factors, agents acting on capillary circulation and/or microcirculation, agents inhibiting vascular permeability, agents acting on cellular metabolism, agents for improving the dermo-epidermal junction, agents inducing head hair and/or body hair growth, lipolysis stimulating agents, slimming agents, anti-cellulite agents, sunscreens, agents capable of reducing or treating bags under the eyes, and mixtures thereof, as long as they are physically and chemically compatible with the other ingredients of the composition and especially with the active ingredients of the present invention.

Furthermore, the nature of these additional active substances must not unacceptably alter the benefits of the active ingredients of the invention. These additional active substances may be synthetic or natural, such as plant extracts, or may originate from a biofermentation method.

Such additional active substances may also be selected, according to their chemical composition, from the group comprising: amino sugars, glucosamine, D-glucosamine, N-acetyl-glucosamine, N-acetyl-D-glucosamine, mannosamine, N-acetyl mannosamine, galactosamine, N-acetyl galactosamine, vitamin B3 and its derivatives, niacinamide, sodium dehydro-acetate, dehydroacetic acid and its salts, phytosterols, salicylic acid compounds, hexamidines, dialkanoyl dihydroxyproline compounds, extracts and derivatives of soya, equol, isoflavones, flavonoids, phytantriol, farnesol, geraniol, bisabolol, peptides and their derivatives, di-, tri-, tetra-, penta-, and hexapeptides and their derivatives, lys-thr-thr-lys-ser, palmitoyl-lys-thr-thr-lys-ser, carnosine, N-acyl amino acid compounds, retinoids, retinyl propionate, retinol, retinyl palmitate, retinyl acetate, retinal, retinoic acid, water soluble vitamins, ascorbates, vitamin C, ascorbyl glucoside, ascorbyl palmitate, magnesium ascorbyl phosphate, sodium ascorbyl phosphate, vitamins and their salts and derivatives, provitamins and their salts and derivatives, ethyl panthenol, vitamin A and its derivatives, vitamin B and its derivatives, vitamin BI, vitamin B2, vitamin B6, vitamin B12, vitamin E, vitamin F, vitamin K and its derivatives, pantothenic acid pantothenyl ethyl ether, panthenol and its derivatives, ethyl panthenol, dexpanthenol, biotin, amino acids and their salts and derivatives, water-soluble amino acids, asparagine, alanine, indole, glutamic acid, water-insoluble vitamins, beta-ionol, cedrol, and their derivatives, water-insoluble amino acids, tyrosine, tryptamine, particulate materials, butylated hydroxytoluene, butylated hydroxyanisole, allantoin, tocopherol nicotinate, tocopherol, tocopherol esters, palmitoyl-gly-his-lys, phytosterol, hydroxy acids, glycolic acid, lactic acid, lactobionic acid, keto acids, pyruvic acid, phytic acid, lysophosphatidic acid, stilbenes, cinnamates, resveratrol, kinetin zeatin, dimethylaminoethanol, natural peptides, soy peptides, acid sugar salts, manganese gluconate, zinc gluconate, piroctone olamine, 3,4,4'-trichlorocarbanilide, triclocarban, zinc pyrithione, hydroquinone, kojic acid ascorbic acid, magnesium ascorbyl phosphate, ascorbyl glucoside, pyridoxine, aloe vera, terpene alcohols, allantoin, bisabolol, dipotassium glycyrrhizinate, glycerol acid, sorbitol, pentaerythritol, pyrrolidone and its salts, dihydroxyacetone, erythrulose, glyceraldehyde, tartaraldehyde, clove oil, menthol, camphor, *eucalyptus* oil, eugenol, menthyl lactate, witch hazel distillate, eicosene copolymer and vinyl pyrrolidone, iodopropyl butylcarbamate, polysaccharide, essential fatty acid, salicylate, glycyrrhetinic acid, carotenoids, ceramides and pseudoceramides, complex lipid, oils in general of natural origin such as shea butter, apricot oil, evening primrose oil, prune oil, palm oil, monoi oil, kahai oil, hydroquinone, HEPES, procysteine, O-octanoyl-6-D-maltose, disodium salt of methyl glycine diacetic acid, steroids such as diosgenin and DHEA derivatives, DHEA dehydroepiandrosterone and/or a chemical or biological precursor or derivative, N-ethylcarbonyl-4-para-aminophenol, alpha hydroxy acids, beta hydroxy acids, moisturisers, epidermal hydrolytic enzymes, plant extracts, phytohormones, yeast extracts, a metalloproteinase inhibitor, enzymes, enzyme inhibitors, enzyme inducers, coenzymes, chelating agents, plant extracts and plant derivatives, essential oils, marine extracts, agents originating from a biofermentation and/or biotechnology method, mineral salts, cell extracts.

Examples include:

- the peptides commercially known as MATRIXYL®, ARGIRELINE®, CHRONOGEN™, LAMINIXYL IS™, PEPTIDE Q10™, COLLAXYL™ (patent FR2827170, ASHLAND®), PEPTIDE VINCI 01™ (patent FR2837098, ASHLAND®), PEPTIDE VINCI 02™ (patent FR2841781, ASHLAND®), ATPeptide™ (patent FR2846883, ASHLAND®) or the synthetic peptide of sequence Arg-Gly-Ser-NH2, marketed under the name ATPeptide™ by ASHLAND®;
- *Artemia salina* extract, marketed under the name GP4G™ (FR2817748, ASHLAND®);
- plant peptide extracts such as flax extracts (Lipigenin™, patent FR2956818, ASHLAND®), extracts of soya, spelt, vine, rape, flax, rice, maize, pea, cocoa;
- yeast extracts, for example Dynagen™, (patent FR2951946, ASHLAND®) or Actopontin™ (patent FR2944526, ASHLAND®).

Uses

A final subject of the invention concerns the use; the compositions according to the present invention are particularly intended for the care of healthy skin, the scalp and of the appendages.

The invention relates more particularly to the cosmetic use of the composition according to the invention to improve the appearance of the skin, to combat the signs of skin ageing or to improve skin hydration and reinforce the barrier function.

The invention further relates to the cosmetic use of a composition according to the invention for soothing the skin.

The invention also relates to the cosmetic use of a composition according to the invention to increase the expression of CB2 endocannabinoid receptors in the skin.

The invention also relates to the cosmetic use of a composition according to the invention to decrease the expression of TRPV1 endocannabinoid receptors in the skin, after irradiation with UVB.

The expression "soothing the skin" means reducing discomfort, such as possible tingling, itching, feeling of warmth, which are the discomforts associated with sensitive and dry skin when the skin is nevertheless considered healthy. Soothing the skin also means reducing the visible signs of sensitive skin such as redness or flaking due to dry skin, as well as other noticeable signs of sensitive skin such as skin that is less smooth and less soft to the touch.

The expression "improving the appearance of the skin" means that the grain of the skin appears finer, more regular.

The expression "signs of skin ageing" means changes in the external appearance of the skin due to ageing such as wrinkles and fine lines, deeper lines, bags under the eyes, dark circles, dullness, loss of elasticity, firmness and/or tone of the skin, irregularity of the skin texture or complexion, but also all internal modifications of the skin which do not systematically result in a modified external appearance such as, for example, thinning of the skin, or all internal degradations of the skin following environmental stresses such as pollution and UV rays.

The expression "improving the barrier function" means that the skin's protective properties against external aggressions (UV radiation, pollution, microorganisms, etc.) are improved.

The expression "improved skin hydration" refers to any improvements in changes in the external appearance of the skin due to dehydration, such as dryness, tightness and discomfort.

EXAMPLES

The present invention will now be illustrated by means of the following examples:

Example 1: Preparation of a Patchouli Extract According to the Invention

For the examples, *Pogostemon cablin* plants were grown in Colombia.

Permits: The applicants inquired about the need to obtain a Research and Commercialisation permit from the Colombian government to access *Pogostemon cablin*'s genetic resources and were informed that no permit was required.

The leaves were harvested, dried and then cryogenically ground in a knife mill with a 4 mm grid, resulting in a powder with a particle size of 400-500 μm. The powder obtained was placed in a stainless steel cartridge, which was placed in a supercritical fluid extractor. The solvent used for extraction was carbon dioxide in the supercritical state and 70% ethanol (70% in water volume/volume) as a polar co-solvent. The ratio of carbon dioxide to ethanol was 15. The pressure in the extractor was 400 bar. The extraction temperature was 50° C. The extract obtained was decoloured with activated carbon, filtered and the ethanol was then evaporated. The extraction yield was 6%.

The pasty extract, the subject of the present invention, was solubilised in agro-sourced octyldodecanol in order to obtain a clear and fluid solution containing between 2 and 6% of crude extract of patchouli leaves.

The resulting solubilised extract, also the subject of the present invention, was a liquid, translucent, pale yellow solution. Its odour was characteristic and the profile obtained by GPC clearly showed the presence of the volatile compounds of *Pogostemon cablin*. The HPLC/DEDL profile shows the presence of phenolic and lipid compounds characteristic of our extract. The overall content of phenolic compounds determined by HPLC via an internal calibration with gallic acid was 0.14%.

Example 2: Characterisation of the Crude Patchouli Extract Obtained According to Example 1

The crude extract was subjected to two successive molecular distillation steps to separate the volatile compounds, found in the distillate, from the phenolic and lipid compounds, found in the residue. The distillate was kept for the study of volatile compounds by GPC. It constitutes fraction A.

The residue was then deposited on a silica column, the size of which was adapted to the mass of extract to be purified. The compounds of interest were separated by flash chromatography using a gradient of solvents ranging from 100% heptane to 100% ethyl acetate. A rinse phase with methanol completed the elution. The contents of the collection tubes containing compounds of the same family were grouped together and the solvents were removed in the rotary evaporator. This fractionation resulted in a rich fraction (fraction B) dissociated from the lipid fraction (fraction C). Each of these fractions was then subjected to a more refined fractionation by preparative HPLC on a C18 column in order to isolate each compound independently. The joint study of NMR spectra and/or mass spectrometry data allowed the identification of several compounds. These were confirmed by the injection of a standard when possible. The non-exhaustive list of compounds present in each of the fractions is presented in the following table 2:

| Chemical family | Identification |
|---|---|
| Volatile compounds (in particular sesquiterpenes and sesquiterpene alcohols) Fraction A | Beta patchoulene |
| | Beta caryophyllene |
| | Seychellene |
| | Alpha guaiene |
| | Alpha patchoulene |
| | Alpha bulnesene |
| | Norpatchoulenol |
| | Patchoulol |
| | Pogostol |
| Phenolic compounds (in particular flavonoids) - Fraction B | Rhamnetine |
| | Rhamnazine |
| | Pachypodol |
| | Retusine |
| | 4',5-dihydroxy-3',7-dimethoxyflavanone |
| | 3,5-dihydroxy-4',7-dimethoxyflavone |
| | 5-hydroxy-7,3',4'-trimethoxyflavanone |
| | 5-hydroxy-3,4',7'-trimethoxyflavone |
| Lipid compounds (in particular tatty acids, sterols, triterpenes, acyl glycerides) - Fraction C | Linolenic acid |
| | Oleanolic acid |
| | Linoleic acid |
| | Methyl linoleate |
| | Palmitic acid |
| | Oleic acid |
| | Stearic acid |
| | Beta sitosterol |
| | Stigmasterol |
| | Acyl glycerides |

It was possible to quantify some markers of the crude extract. This contained in particular:

20.9% patchoulol co-eluted with pogostol (Fraction A)

13.2% of α-bulnesene (Fraction A)

9.0% of α-guaiene (Fraction A)

1.8% pachypodol co-eluted with 5-hydroxy-7,3',4'-trimethoxyflavanone (Fraction B)

Example 3: Production of an Essential Oil-Type Patchouli Extract

Conventionally, patchouli essential oil is extracted by steam distillation. The aerial parts (leaves and stems) of patchouli are cut and dried, then placed in stills and a stream of steam is passed through them; this steam releases the volatile molecules or essential oil which is carried away by the steam and condenses in the condenser. As the essential oil is generally less dense than water and is not water-soluble or only slightly water-soluble, it is collected at the outlet in a decanter called an essencier. The water that still contains trace amounts of essential oil is called hydrolate and can be used as an aromatic solution.

Patchouli essential oil is a more or less viscous liquid ranging from yellow to reddish brown. The patchoulol content is between 27 and 35% according to the ISO standard 2003.

Example 4: Identification of Major Phytochemical Differences Between an Essential Oil and the Extract Obtained According to Example 1

There is extensive prior art regarding the compounds constituting a Patchouli essential oil. To our knowledge, the presence of flavonoids or lipids in these essential oils has never been reported (The essential oil of patchouli, *Pogostemon cablin*: A review, *Flavour Fragr J.* 2017; 1-46.)

Figure 5:
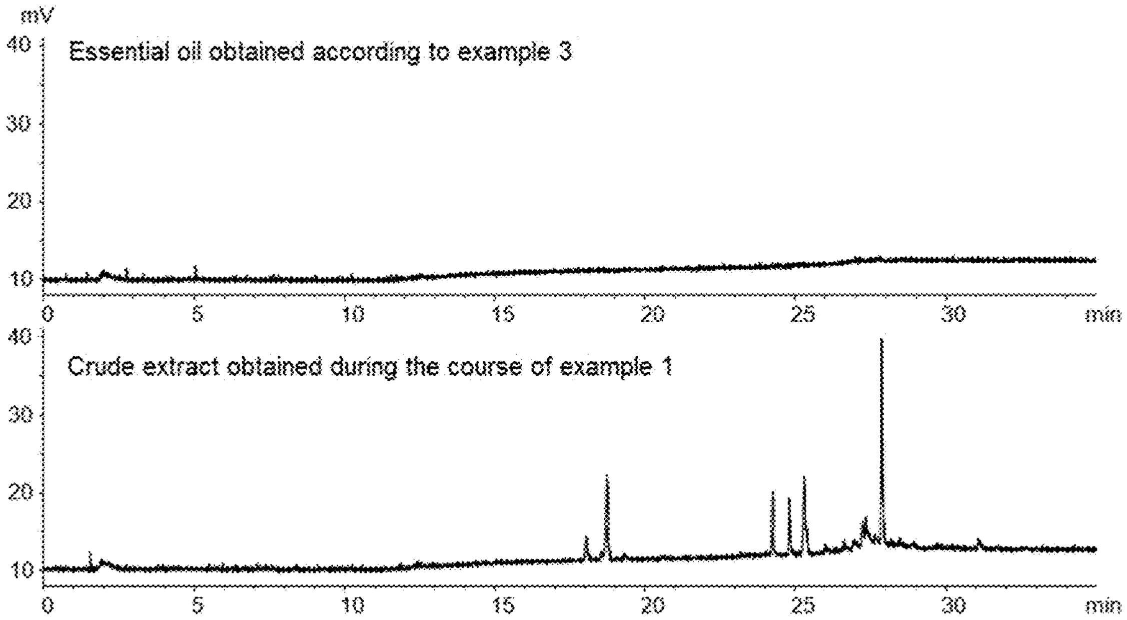

The crude patchouli extract obtained in example 1 was analysed in parallel with an essential oil obtained in example 3, by liquid chromatography coupled with a DEDL detector at the same concentration. The separation is done on an RP-C18 column in gradient elution mode with acidified mixtures of water/acetonitrile (ACN) over path A and acetonitrile/isopropanol (IPA) over path B for a duration of 35 minutes. Under these conditions, phenolic compounds are detected between 17 and 21 minutes while lipid compounds elute after 23 minutes. As shown in FIG. 5, phenolic and lipid compounds are not detected in an essential oil (obtained according to example 3).

Example 5: Evaluation of the Effect of the Patchouli Extract Prepared According to Example 1 on Collagen I Synthesis in Ex Vivo Skin Biopsies The aim of this study is to show the effect of patchouli extract prepared according to example 1 on the synthesis of collagen I in biopsies of healthy skin. Indeed, a reduction in the level of this collagen is linked to the atrophy of the dermal extracellular matrix during skin ageing.

Protocol: Collagen I is assessed by immunohistochemistry. Biopsies of healthy human skin in culture are treated with patchouli extract obtained according to example 1 and formulated at 1% (mass/mass) in a cream applied twice a day for 48 hours topically (20 µl/biopsy). The formulation of the cream is given in Table 3 below. Control biopsies received a placebo cream. The formulas used were classic oil-in-water emulsions.

The detection of collagen I was then carried out by immunostaining with a specific antibody.

This technique was performed using paraffin sections incubated in the presence of anti-collagen I antibody (rabbit polyclonal, Abcam). After an hour and a half of incubation followed by rinses, the sections were incubated in the presence of the secondary anti-rabbit antibody coupled with a fluorophore (Alexa Fluor® 488, Invitrogen). The sections were then examined under an Epi-fluorescence microscope (Zeiss Axiovert 200M microscope). Collagen I expression was then observed and quantified by image analysis (Volocity® image analysis software, Improvision).

TABLE 3

| List of ingredients (Trade name \| INCI) | | % (weight/ weight) | Supplier |
|---|---|---|---|
| phase A | | | |
| Purified Water | Water/Aqua | Qs. 100 | Local |
| EDTA tetrasodium salt | Tetrasodium EDTA | 0.05 | Fisher |
| Lubrajel* MS Free hydrogel | Glycerin (and) Glyceryl Acrylafe/Acrylic Acid Copolymer (and) Phenoxyethanol | 3.00 | Ashland |
| LiquaPar ™/Rokonsal ™ MEP preservative | Phenoxyethanol (and) methylparaben (and) ethylparaben (and) propylparaben | 1.00 | Ashland |
| phase B | | | |
| UltraThix ™ P-100 polymer | Acrylic Acid/VP Crosspolymer | 0.60 | Ashland |
| phase C | | | |
| Sodium Hydroxide | Sodium Hydroxide | 0.02 | Fisher |
| Purified Water | Water/Aqua | 0.50 | Local |
| phase D | | | |
| Belsil* W3230 | Bis-stearoxydimethylsilane (and) stearyl alcohol (and) dimethicone | 2.00 | Wacker |
| Simulsol* 165 | PEG-100 stearate (and) glyceryl stearate | 2.00 | Seppic |
| Refined Shea Butter | *Butyrospermum Parkii* (Shea) Butter | 2.00 | Ashland |
| Ceraphyl ™ 28 ester | Cetyl lactate | 1.50 | Ashland |
| Ceraphyl 791 ester | Isocetyl stearoyl stearate | 2.00 | Ashland |
| Ceraphyl ODS ester | Octyldodecyl stearate | 3.00 | Ashland |
| Ceraphyl 368 ester | Ethylhexyl palmitate | 4.00 | Ashland |
| Patchouli extract according to example 1I | | 1.00 | Ashland |
| phase E | | | |
| Sodium Hydroxide | Sodium Hydroxide | 0.03 | Fisher |
| Purified Water | Water/Aqua | 0.50 | Local |
| phase F | | | |
| total | | 100.00% | |

Results:

Treatment with 1% patchouli extract showed an increase in collagen I labelling intensity in skin biopsies at 48 hours (+54%, highly significant compared to biopsies treated with the placebo cream).

Conclusion

Patchouli extract at 1% was able to increase the level of collagen I, which is decreased during ageing, in healthy skin biopsies ex vivo.

Example 6: Evaluation of the Effect of the Patchouli Extract Prepared According to Example 1 on CB2 Cannabinoid Receptors in Ex Vivo Skin Biopsies The aim of this study was to show the effect of the patchouli extract prepared according to example 1 on cannabinoid CB2 receptors in biopsies of healthy skin.

CB2 receptors are part of the endocannabinoid system in the skin. Both endocannabinoids and exogenous cannabinoids can act on these receptors. CB2 receptor agonists are linked to anti-inflammatory and pain-relieving effects.

Protocol:

CB2 receptors are studied by immunohistochemistry. Biopsies of healthy skin were treated for 48 hours with a cream whose formula is given in Table 3, containing or not (in the case of the placebo) the 1% patchouli extract (20 μl per biopsy). After this treatment, the biopsies were fixed with different solvents and then embedded in paraffin. Sections measuring 6 μm were made, then incubated with a first antibody specific to CB2 receptors (rabbit polyclonal, Thermofisher) for one and a half hours. After successive rinses, the sections were incubated in the presence of the secondary anti-rabbit antibody coupled to a fluorophore (Alexa Fluor® 488, Invitrogen). The sections were then examined under an Epi-fluorescence microscope (Zeiss Axiovert 200M microscope). CB2 expression was then observed and quantified by image analysis (Volocity® image analysis software, Improvision).

Results:

In the skin biopsies treated with the patchouli extract according to example 1, an increase in CB2 labelling intensity was observed. This increase was +20% with the 0.1% extract and +36% with the 1% extract, compared to the biopsies treated with the placebo cream.

Conclusion

The patchouli extract obtained according to example 1 was able to increase the expression of CB2 cannabinoid receptors in healthy skin biopsies ex vivo. The effect of patchouli on CB2 receptors may be associated with a decrease in inflammation in healthy, stressed and fragile skin.

Example 7: Evaluation of the Soothing Effect of the Patchouli Extract Following UVB Stress The aim of this study was to evaluate the effect of the patchouli extract obtained according to example 1 on the inflammatory status of healthy skin subjected to UVB irradiation. Inflammation was assessed by characterisation of IL1-R1, the receptor for interleukin-1, this interleukin and its receptor being increased in UVB-induced inflammation. A decrease in IL1-R1 in skin biopsies exposed to UVB stress will therefore make it possible to evaluate a soothing effect of the patchouli extract. In the same type of experiment, the effect of the patchouli extract obtained according to example 1 will be compared to that of a patchouli essential oil at the equivalent dilution of 1%, obtained according to example 3.

Protocol:

Biopsies of healthy skin in culture are exposed to UVB irradiation at 200 mJ/cm2. Then, the cream containing, or not in the case of the placebo, the 0.5 and 1% patchouli extract, prepared according to example 1 and formulated in a cream according to the formula given in table 3, was applied to the biopsies (20 μL per biopsy). In parallel, a series of biopsies is treated with an identical cream but formulated with 1% patchouli essential oil instead of the extract according to example 1. After 48 hours of treatment, the biopsies are fixed with different solvents and then embedded in paraffin. Sections of 6 μm were taken and incubated with a first antibody specific for interleukin-1 receptors (rabbit polyclonal IL1-R1, Tebu Rockland) for two hours. After successive rinses, the sections were incubated in the presence of the secondary anti-rabbit antibody coupled to a fluorophore (Alexa Fluor® 488, Invitrogen). The sections were then examined under an Epi-fluorescence microscope (Zeiss Axiovert 200M microscope). IL1-R1 expression was then observed and quantified by image analysis (Volocity® image analysis software, Improvision).

Figure 2:
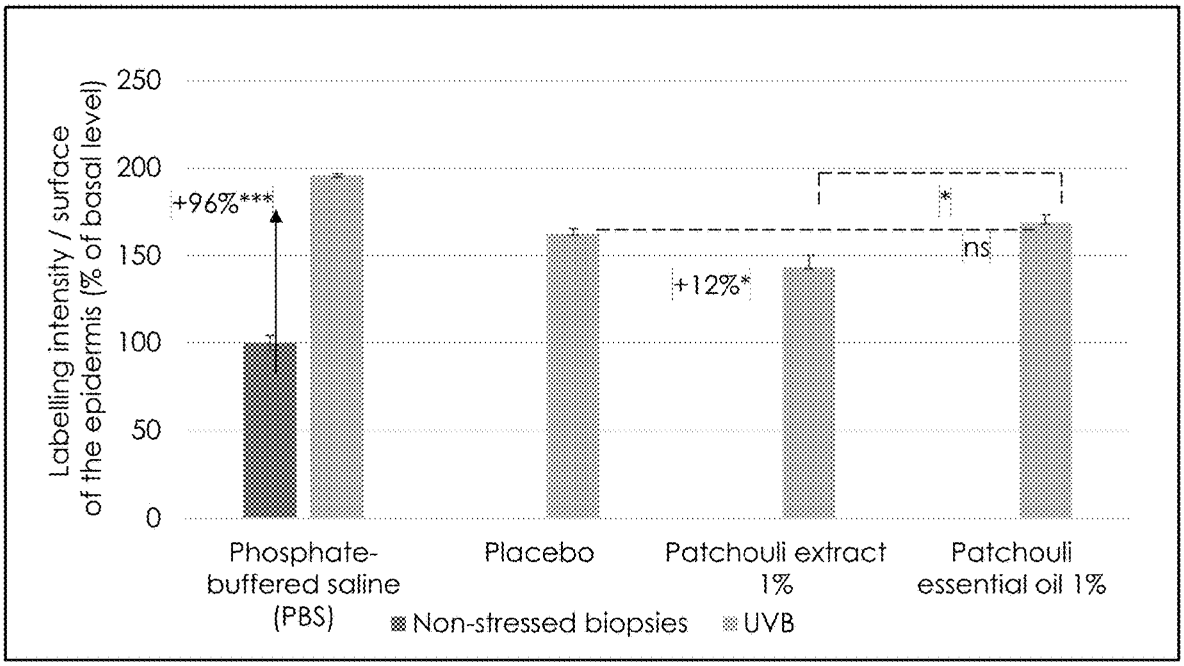
FIG. 2 shows the results obtained with the patchouli extract and patchouli essential oil on the level of IL1-R1 assessed on skin biopsies after UVB irradiation FIG. 3—Quantification of IL1-R1 (interleukin-1 receptor) labelling on skin biopsies exposed to bacterial lipopolysaccharide and treated with patchouli extract

Results:

Exposure of ex vivo skin biopsies to UVB generated an increase in IL1-R1 labelling, indicating an inflammatory state of the skin. In biopsies irradiated and treated with the patchouli extract cream, IL1-R1 levels were lower compared to placebo. A dose-dependent effect was observed between 0.5% and 1% patchouli extract in the cream (−9% and −17%, respectively, FIG. 1). The cream formulated with 1% patchouli essential oil led to a non-significant effect compared to placebo (FIG. 2).

Conclusion

Patchouli extract at 0.5 and 1% significantly decreased IL1-R1 levels in UVB-irradiated healthy skin biopsies, revealing a decreased level of inflammation, and therefore a potential soothing effect of the extract, in a significantly different way to patchouli essential oil.

Example 8: Evaluation of the Soothing Effect of the Patchouli Extract Following Stress Induced by Bacterial Lipopolysaccharide (LPS)

The aim of this experiment was to test the soothing effect of the patchouli extract obtained according to example 1 on skin biopsies exposed to bacterial stress. To do this, the biopsies were incubated in the presence of lipopolysaccharide (LPS) of bacterial origin, an antigenic compound that induces an inflammatory type response.

Protocol:

Cultured healthy skin biopsies were incubated in the presence of 0.5 mg/ml LPS overnight. Then, the cream containing, or not in the case of the placebo, 1% patchouli extract, prepared according to example 1, was applied to the biopsies (20 μL per biopsy). The formula of the cream is given in Table 3. After 48 hours of treatment, the biopsies are fixed with different solvents and then embedded in paraffin. Sections of 6 μm were taken and incubated with a first antibody specific for interleukin-1 receptors (rabbit polyclonal IL1-R1, Tebu Rockland) for two hours. After successive rinses, the sections were incubated in the presence of the secondary anti-rabbit antibody coupled to a fluorophore (Alexa Fluor® 488, Invitrogen). The sections were then examined under an Epi-fluorescence microscope (Zeiss Axiovert 200M microscope). IL1-R1 expression was then observed and quantified by image analysis (Volocity® image analysis software, Improvision).

Figure 3:
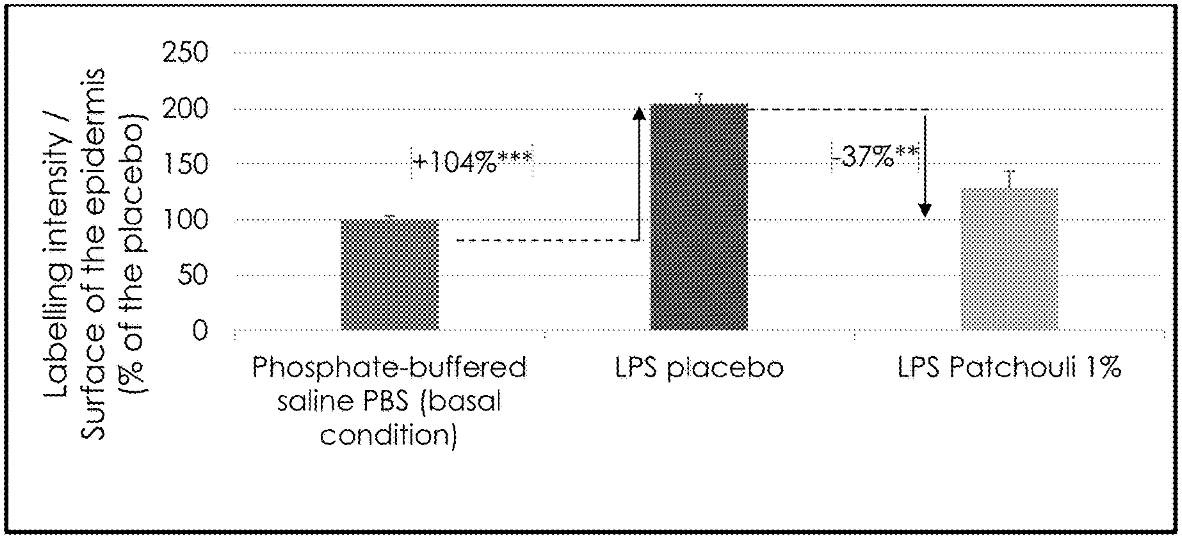
FIG. 3 shows the results obtained with patchouli extract on the level of IL1-R1 assessed on skin biopsies exposed to bacterial lipopolysaccharide FIG. 4—Quantification of TRPV1 labelling on skin biopsies exposed to UVB and treated with patchouli extract

Results:

Exposure of ex vivo skin biopsies to bacterial LPS generated an increase in IL1-R1 labelling, revealing an inflammatory state of the skin. In LPS-stressed biopsies treated with the patchouli extract cream, IL1-R1 levels were lower (−37%, highly significant compared to LPS-stressed biopsies treated with placebo cream) (FIG. 3).

Conclusion

Patchouli extract at 1% significantly decreased the level of IL1-R1 in biopsies of healthy skin exposed to bacterial stress, revealing a decreased level of inflammation, and therefore a potential soothing effect of the extract in the face of bacterial aggression.

Example 9: Evaluation of the Effect of the Patchouli Extract on the TRPV1 Receptor Following UVB Irradiation Endocannabinoids and CB1 and CB2 cannabinoid receptor agonists may exert their anti-inflammatory effect by acting on other receptors such as TRPV1 (Transient Receptor Potential Vanilloid 1) associated with nociception and pruritus (Michael J. Caterina. TRP Channel Cannabinoid Receptors in Skin Sensation, Homeostasis, and Inflammation. ACS Chem. Neurosci. 2014, 5, 1107-1116).

The Transient Receptor Potential Vanilloid 1 (TRPV1) receptor acts as a detector of various stresses associated with pain perception (nociception), including heat, pH decrease, as well as activation by endogenous proinflammatory mediators. Its activation results in an inflammatory reaction, which may be accompanied by a perception of discomfort, itching, as in the case of pruritus, or even a painful sensation.

TRPV1 is a receptor for exogenous endocannabinoids and cannabinoids, which can exert an analgesic effect (Michael J. Caterina. TRP Channel Cannabinoid Receptors in Skin Sensation, Homeostasis, and Inflammation. *ACS Chem. Neurosci.* 2014, 5, 1107-1116).

In the present study, the effect of the patchouli extract obtained according to example 1 on TRPV1 receptors was evaluated on cultured skin biopsies exposed to UVB stress.

Protocol:

Biopsies of healthy skin in culture are exposed to UVB irradiation at 200 mJ/cm2. Then, the cream containing, or not in the case of the placebo, 1% patchouli extract, prepared according to example 1, was applied to the biopsies (20 μL per biopsy). The formula of the cream is given in Table 3. After 48 hours of treatment, the biopsies are fixed with different solvents and then embedded in paraffin. Sections measuring 6 μm were taken and incubated with a first antibody specific for TRPV1 receptors (rabbit polyclonal, Invitrogen) for two hours. After successive rinses, the sections were incubated in the presence of the secondary anti-rabbit antibody coupled to a fluorophore (Alexa Fluor® 488, Invitrogen). The sections were then examined under an Epi-fluorescence microscope (Zeiss Axiovert 200M microscope). TRPV1 expression was then observed and quantified by image analysis (Volocity® image analysis software, Improvision).

Figure 4:
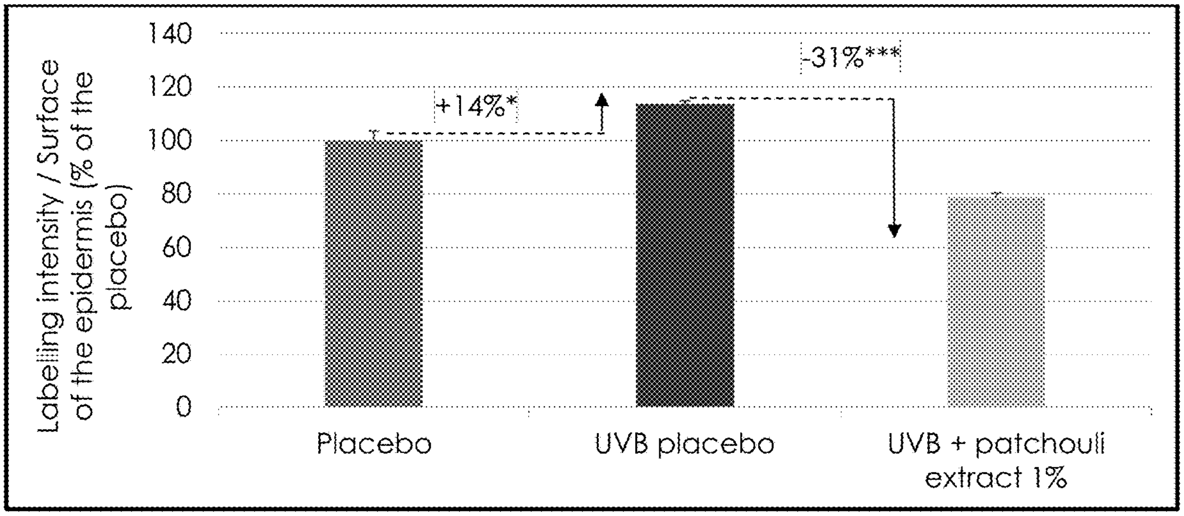
FIG. 4 shows the results obtained with patchouli extract on the TRPV1 receptor, associated with the response to cannabinoids, on skin biopsies exposed to UVB irradiation FIG. 5—Chromatographic profiles of patchouli essential oil obtained according to example 3 and the patchouli crude extract from example 1, in HPLC/DEDL on an RP-C18 column with gradient elution (0-8 min 100% A, 8-25 min change from 100% A to 100% B then 25-35 min 100% B—A: H2O/ACN/HCO2H 95/5/0.1 (v:v:v) and B: IPA/ACN/HCO2H 80/20/0.1 (v:v:v)). The y-axis shows the detector response in mV and the x-axis shows the analysis time in minutes.

Results:

Skin biopsies exposed to UVB stress showed an increase in TRPV1 labelling which, according to the literature, is associated with an increase in the inflammatory state. In skin biopsies treated with the patchouli extract obtained according to example 1, a decrease in TRPV1 labelling intensity was observed, indicating a reduction in the UVB-induced inflammatory state (−31%, highly significant compared to the UVB-irradiated biopsies treated with the placebo cream) (FIG. 4).

Conclusion

Treatment of healthy skin biopsies with patchouli extract showed a reduction in TRPV1 expression in UVB-irradiated healthy skin, associated with a decrease in inflammation and skin sensitivity.

Example 10: Evaluation of the Effect of the Patchouli Extract Prepared According to Example 1 on Loricrin Synthesis in Ex Vivo Skin Biopsies The aim of this study is to show the effect of patchouli extract prepared according to example 1 on the synthesis of loricrin in biopsies of healthy skin. Indeed, this protein is involved in the process of epidermal differentiation and thus participates in the elaboration of the skin barrier, in conjunction with skin hydration.

Protocol:

Loricrin was assessed by immunohistochemistry. Biopsies of healthy human skin in culture were treated with patchouli extract obtained according to example 1 and formulated at 0.5% (mass/mass) in a cream applied twice a day for 48 hours topically (20 μl/biopsy). The formula of the cream is given in Table 3. Control biopsies received a placebo cream. The formulas used were classic oil-in-water emulsions.

The detection of loricrin is then carried out by immunostaining with a specific antibody.

This technique is performed using paraffin sections incubated in the presence of anti-loricrin antibody (rabbit polyclonal, Abcam). After an hour and a half of incubation followed by rinses, the sections were incubated in the presence of the secondary anti-rabbit antibody coupled with a fluorophore (Alexa Fluor® 488, Invitrogen). The sections were then examined under an Epi-fluorescence microscope (Zeiss Axiovert 200M microscope). Loricrin expression was then observed and quantified by image analysis (Volocity® image analysis software, Improvision).

Results:

Treatment with patchouli extract at 0.5% showed an increase in loricrin labelling intensity in skin biopsies at 48 hours (+39%, highly significant compared to biopsies treated with the placebo cream).

Conclusion

The patchouli extract increased loricrin levels in healthy skin biopsies ex vivo, in relation to an effect on epidermal differentiation and skin barrier function.

What is claimed is:

1. A method of cosmetic treatment comprising topically applying to a skin, a scalp, or appendages a composition comprising a physiologically acceptable medium and, as an active substance, a solubilized patchouli extract obtained by a process comprising:

a) harvesting an upper part of patchouli aerial parts and then drying, and grinding or cryogenically grinding;

b) performing a supercritical carbon dioxide extraction in presence of a polar co-solvent, said polar co-solvent being ethanol at a concentration of between 50 and 96% volume/volume percentage;

c) recovering a crude patchouli extract and decolouring in presence of activated carbon and filtering before the co-solvent is evaporated;

d) solubilizing the crude patchouli extract obtained in c) in a saturated or unsaturated, linear or branched fatty alcohol solvent comprising 8 to 30 carbon atoms to obtain a crude extract concentration in the solubilized crude patchouli extract between 2 and 6% by weight of a total weight of the solubilized patchouli extract, for care of the skin, the scalp, or the appendages, wherein the solubilized crude patchouli extract has a property of: combatting signs of skin ageing, wherein the solubilized crude patchouli extract obtained from a) to c) comprises: 60 to 70% of volatile compounds, mainly sesquiterpenes and sesquiterpene alcohols, wherein said volatile compounds comprise 16.1% to 25.7% patchoulol co-eluted with pogostol; from 26 to 32% of lipid compounds selected from a group consisting of fatty acids, phytosterols, triterpenes, acyl glycerides; and from 3 to 4% of phenolic compounds primarily flavonoids.

2. The method of cosmetic treatment according to claim 1, wherein the solubilized crude patchouli extract has a further property of increasing the expression of cannabinoid type 2 (CB2) endocannabinoid receptors in the skin.

3. The method of cosmetic treatment according to claim 1, wherein the solubilized crude patchouli extract has a further property of decreasing expression of transient receptor potential vanilloid 1 (TRPV) 1 endocannabinoid receptors in the skin, after ultraviolet B (UVB) irradiation.

4. The method according to claim 1, wherein in b), the ethanol is at a concentration between 60 and 80% volume/volume percentage.

5. The method according to claim 1, wherein in b), a weight ratio of supercritical carbon dioxide to ethanol is 15:1 and a weight ratio of supercritical carbon dioxide to a quantity of raw material used is between 10 and 70.

6. The method according to claim 1, wherein in b), an extraction temperature is between 5° and 60° C., and a pressure within an extractor is between 230 and 700 bar.

7. The method according to claim 1, wherein the composition comprises the solubilized crude patchouli extract at a concentration between 0.1 and 10%, by weight in relation to a total weight of the composition.

* * * * *